(12) United States Patent
Hines et al.

(10) Patent No.: US 10,228,494 B2
(45) Date of Patent: *Mar. 12, 2019

(54) LENS PROTECTION SYSTEMS

(71) Applicant: RIPCLEAR LLC, Jackson Heights, NY (US)

(72) Inventors: Zachary Hines, Jackson Heights, NY (US); Ryan Doherty, Bend, OR (US)

(73) Assignee: RipClear LLC, Jackson Heights, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,973

(22) Filed: Aug. 18, 2016

(65) Prior Publication Data

US 2017/0052286 A1    Feb. 23, 2017

Related U.S. Application Data (63) Continuation of application No. 14/828,408, filed on Aug. 17, 2015, now Pat. No. 9,442,306.

(51) Int. Cl.
| | |
|---|---|
| *G02B 1/14* | (2015.01) |
| *G02C 7/10* | (2006.01) |
| *A61F 9/02* | (2006.01) |
| *G02B 1/04* | (2006.01) |
| *G02C 7/02* | (2006.01) |
| *G02C 9/00* | (2006.01) |

(52) U.S. Cl.
CPC .............. *G02B 1/14* (2015.01); *A61F 9/025* (2013.01); *G02B 1/04* (2013.01); *G02C 7/02* (2013.01); *G02C 7/104* (2013.01); *G02C 9/00* (2013.01); *G02C 2202/16* (2013.01)

(58) Field of Classification Search
CPC . G02C 3/00; G02C 3/003; G02C 3/02; G02C 7/10; G02C 7/104; G02C 7/16; G02C 9/00; G02C 9/04; G02C 13/006; G02C 2202/16; G02C 5/001; A61F 9/025; A61F 9/022; G02B 1/14
USPC ....... 351/44, 47, 159.57, 159.69, 178; 2/434
See application file for complete search history.

(56) References Cited

U.S. PATENT DOCUMENTS

| | | | |
|---|---|---|---|
| 2,511,329 A * | 6/1950 | Craig | ..................... A61F 9/022 2/12 |
| 2,923,944 A | 2/1960 | Lindblom | |
| | | (Continued) | |

FOREIGN PATENT DOCUMENTS

CN          203385951 U      1/2014

OTHER PUBLICATIONS

Poly-Tech Industries, Inc, PET (Thermoplastic Polyester), 2011.*
Canadian Patent Application No. 2,994,857, Office Action dated Oct. 3, 2018, 4 pages.

*Primary Examiner* — Jordan Schwartz
(74) *Attorney, Agent, or Firm* — Leber IP Law; Celia Leber (57) ABSTRACT

The present disclosure features lens protection systems that comprise multi-layer film laminates that include an optically clear protective film, which remains on the lens during use and carrier layers that are used to assist the user with applying the protective film to the lens. These systems are suitable for use with a wide variety of eyewear, including but not limited to ski goggles, tactical goggles, diving goggles, protective eyewear such as safety glasses, sun glasses, helmet visors (e.g., for football, hockey, or motorcycle helmets), and paintball masks.

20 Claims, 13 Drawing Sheets

(56) References Cited

U.S. PATENT DOCUMENTS

| | | | |
|---|---|---|---|
| 4,268,134 A | 5/1981 | Gulati et al. | |
| 4,528,701 A | 7/1985 | Smith | |
| 4,716,601 A * | 1/1988 | McNeal | A61F 9/025 2/434 |
| 6,217,099 B1 | 4/2001 | McKinney et al. | |
| 6,907,617 B2 | 6/2005 | Johnson | |
| 7,070,837 B2 | 7/2006 | Ross | |
| 7,858,001 B2 | 12/2010 | Qin et al. | |
| 8,331,007 B2 | 12/2012 | Chavel et al. | |
| 8,567,596 B1 | 10/2013 | Mason, Jr. | |
| 9,442,306 B1 * | 9/2016 | Hines | G02B 1/14 |
| 2001/0035936 A1 | 11/2001 | Maisnik | |
| 2003/0156499 A1 * | 8/2003 | Miller | G04B 39/00 368/296 |
| 2004/0246386 A1 * | 12/2004 | Thomas | B32B 7/06 348/818 |
| 2005/0260343 A1 | 11/2005 | Han | |
| 2009/0026095 A1 | 1/2009 | Lofland et al. | |
| 2009/0233032 A1 | 9/2009 | Craig | |
| 2011/0043902 A1 * | 2/2011 | Ishibashi | B29D 11/00634 359/359 |
| 2012/0070603 A1 | 3/2012 | Hsu | |
| 2012/0081792 A1 | 4/2012 | Neuffer | |
| 2013/0045371 A1 | 2/2013 | O'Donnell | |
| 2013/0141693 A1 * | 6/2013 | McCabe | G02C 7/104 351/159.56 |
| 2013/0194538 A1 * | 8/2013 | Junkins | G02C 9/04 351/47 |
| 2013/0293959 A1 | 11/2013 | McDonald | |
| 2014/0333891 A1 * | 11/2014 | Boffey | B29D 11/0073 351/159.01 |
| 2015/0131047 A1 * | 5/2015 | Saylor | G02C 7/12 351/44 |
| 2015/0331259 A1 * | 11/2015 | Jiang | B29D 11/0073 351/159.56 |
| 2015/0359675 A1 * | 12/2015 | Wilson | A42B 3/26 2/431 |
| 2015/0376477 A1 * | 12/2015 | Katami | G06F 3/0414 345/173 |
| 2016/0340559 A1 * | 11/2016 | Jiang | G02B 5/3033 |
| 2017/0107369 A1 * | 4/2017 | Kitayama | C08L 33/00 |
| 2017/0166750 A1 * | 6/2017 | Pokorny | C09D 4/00 |
| 2017/0363884 A1 * | 12/2017 | Hallock | A61F 9/022 |

* cited by examiner

LENS PROTECTION SYSTEMS

RELATED APPLICATION

This application is a continuation application of U.S. application Ser. No. 14/828,408, filed Aug. 17, 2015, the entire contents of which is hereby incorporated by reference.

BACKGROUND

Lenses of eyewear, for example goggles used in sports and outdoor activities and protective eyewear (e.g., safety glasses), are subject to scratching and damage. Eyewear is often costly to replace, with even replaceable lenses being expensive to obtain and hard to protect from damage. Moreover, it is inconvenient and in some cases not feasible to continually replace one's eyewear or lenses.

SUMMARY

The present disclosure features lens protection systems, for example, for the protection of eyewear lenses when wearing, retailing, and storing. The systems comprise multi-layer film laminates, which include a protective film that remains on the lens during use, and carrier layers that are used to assist the user with applying the protective film to the lens. In some cases, the protective film includes multiple protective layers adhered together with a pressure sensitive adhesive, allowing successive layers to be peeled off as they become scratched or contaminated, revealing a fresh underlying layer.

These systems are suitable for use with a wide variety of eyewear, including but not limited to ski goggles, prescription goggle lenses, tactical goggles, sun glasses, corrective prescription glasses, diving goggles, protective industrial eyewear such as safety glasses, firefighting protective eyewear, welding shields, helmet visors (e.g., for football, hockey, or motorcycle helmets), and paintball masks. While primarily intended for eyewear, the systems used herein can be utilized to protect other types of lenses such as the lenses of professional grade cameras or video cameras, such as those commercially available from Canon®, Nikon®, or GoPro®. In some implementations the systems are semi-customized, while in other implementations the systems are universally fitted to fit a particular type of eyewear; for example, some systems are shaped to fit within the frame of a ski goggle without obscuring the vents of the goggle, while others are configured to cover a major portion of the surface of the face shield of a helmet.

In some preferred implementations, the protective film that remains on the lens has a very high degree of transparency and light transmission, such that the visual acuity and other optical characteristics obtainable with the eyewear are substantially unchanged by the presence of the layer. Some protective films are configured to allow the lens to which they are applied to pass optical tests such as the ANSI Z87.1-2010 rating or other related tests. In some cases, a lens with the protective film in place will meet the MIL-PRF-32432 Optical Distortion specification, and/or the ANSI Z87.1 haze, prism power, resolving power, refractive power and astigmatism standards.

In some implementations, the protective film is configured to provide optical clarity, while altering other optical characteristics of the lens, e.g., by imparting a tint or mirrored surface to the lens.

In one aspect, the disclosure features an eyewear protection system comprising (a) an optically transparent protective film, shaped to fit within a frame in which an eyewear lens is mounted, and comprising a sheet material carrying a layer of an optically transparent adhesive, the adhesive being configured to removably adhere to a surface of the eyewear lens without leaving a visible residue on the lens when removed therefrom; and (b) an outer carrier layer removably adhered to each side of the protective film.

Some implementations include one or more of the following features.

The outer carrier layers may include an application layer configured to assist a user in applying the sheet material to the lens; and a base layer, configured to provide stiffness to the lens protection system during shipping. The base layer may also be configured to protect the protective film from debris and creasing until the protective film is adhered to the lens The application layer may be adhered to the protective film by a pressure sensitive adhesive carried by the application layer. In some cases, the adhesive carried by the protective film comprises a silicone. The adhesive carried by the protective film may provide a watertight seal against the lens surface. The layer of adhesive carried by the protective film may have a thickness of, for example, about 10 to 30 µm.

The protective film may comprise a polymer selected from the group consisting of thermoplastic urethanes and polyethylene terephthalate polymers. In some cases, the protective film has a thickness of from about 0.01 to 1.0 mm. In implementations in which the protective film is shaped to fit a spherical goggle lens, the protective film may have a thickness of from about 0.1 to 0.3 mm. In some cases, for example when the system is designed for use on a spherical lens, the protective film comprises a thermoplastic urethane. The protective film may carry a scratch resistant coating layer on a surface opposite the surface on which the adhesive is carried, for example to extend the life of the protective film if the protective film is formed of a material that is susceptible to scratching.

In some implementations, the system further includes application tabs extending from the carrier layers. The carrier layers may in some cases be formed of polyethylene terephthalate, but may include or be formed of other materials to meet the requirements of a particular application.

The protective film may include two or more protective layers adhered to each other, e.g., by a pressure sensitive adhesive. The pressure sensitive adhesive adhering the layers together preferably has an adhesion strength that is less than or equal to that of the adhesive adhering the protective film to the lens, so that the successive layers can be removed without removing the protective film from the lens.

The present disclosure also features methods of making and using the systems described herein.

For example, in one aspect the disclosure features a method of protecting an eyewear lens, the method comprising applying an optically transparent protective film to an eyewear lens, the film being shaped to fit within a frame holding the lens, and comprising a sheet material carrying a layer of an optically transparent adhesive, the adhesive being configured to removably adhere to a surface of the eyewear lens without leaving a visible residue on the lens when removed therefrom.

Some implementations of this method include one or more of the following features.

The method steps may be performed by an end user of eyewear including the eyewear lens.

The method may further include, prior to applying the protective film, removing a base layer from the protective film, exposing the adhesive carried by the protective film.

The method may further include, after applying the protective film, removing an application layer from the protective film, the application layer being adhered to the protective film by a pressure sensitive adhesive carried by the application layer.

In preferred embodiments, methods include smoothing the protective film against the lens surface by applying pressure to the application layer prior to removing the application layer. Pressure may be applied starting at or near the center of the lens and moving outwardly.

The method may also include removing the protective film from the lens, e.g., when it has become scratched or contaminated, and applying a new protective film to the lens. In some cases, the protective film comprises a plurality of layers of sheet material, and the method further comprises removing one layer of the protective film to expose an underlying layer.

The disclosure also features kits of accessories that may be supplied with or separately from the eyewear protection systems, e.g., lens cleaning kits.

DETAILED DESCRIPTION

Various eyewear protection systems are described herein, which have in common a laminate that includes carrier layers provided on opposite sides of a protective film that remains on the lens. The protective film may be formed of a single layer or multiple layers, as will be discussed in detail below.

Figure 1:
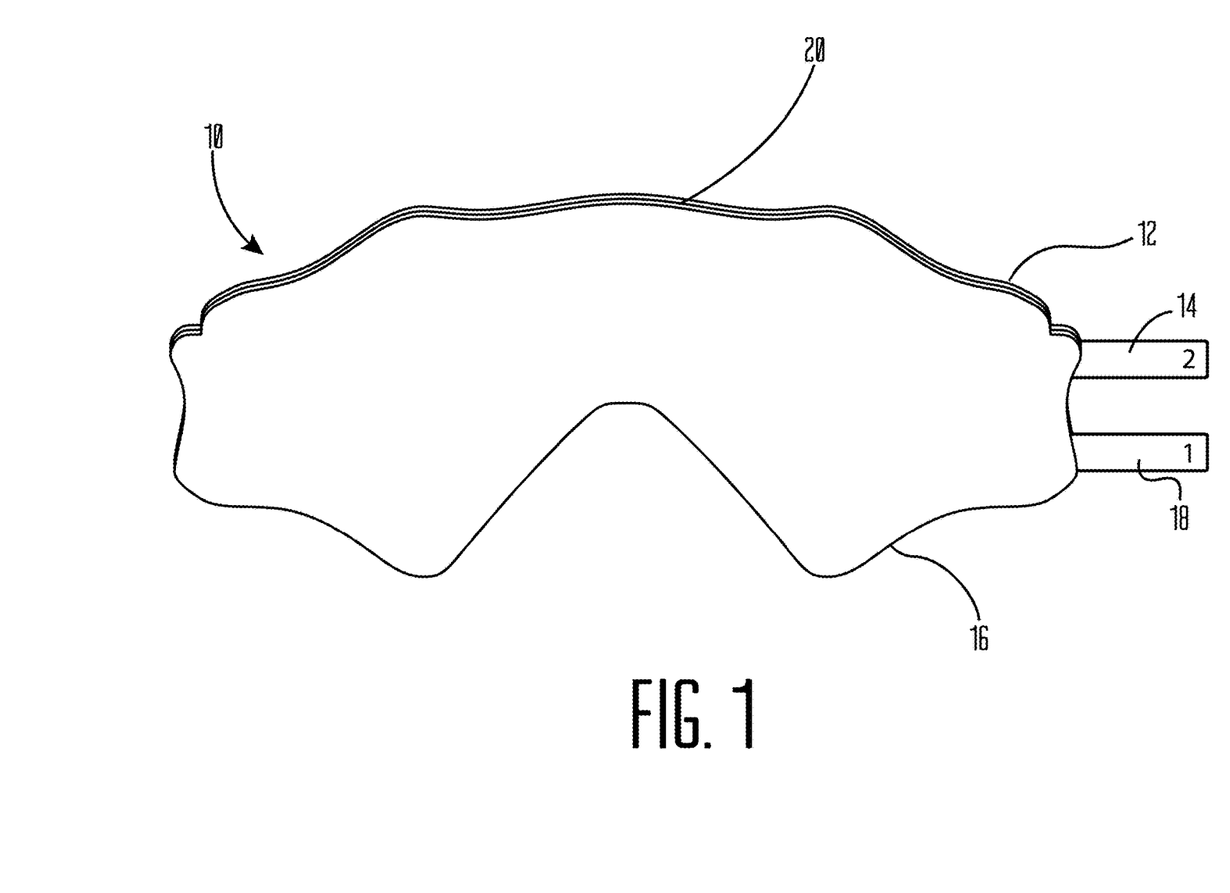
FIG. 1 is a perspective view of an eyewear protection system according to one implementation.
Figure 1A:
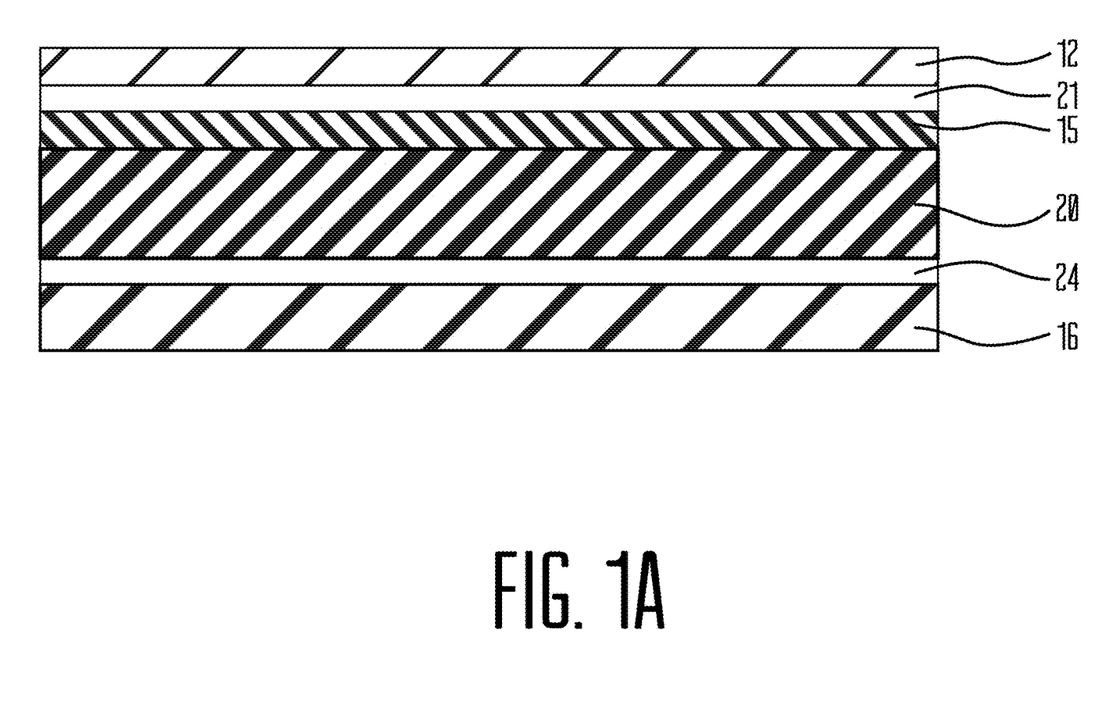
FIG. 1A is a highly enlarged cross-sectional view of the eyewear protection system of FIG. 1.

Referring to FIGS. 1 and 1A, an eyewear protection system 10 according to one implementation includes an application layer 12, having an application tab 14 extending from one corner, a base layer 16, having an application tab 18 extending from one corner, and a protective film 20 interposed between the application layer and base layer. As will be discussed in further detail below, the protective film 20 is applied to the lens and protects the lens during use, while the application layer 12 assists in applying the protective film to the lens (as well as protecting the non-adhesive surface of the protective film during shipping and storage), and the base layer provides support to the other two layers and prevents creasing or other damage to the layers prior to use while also protecting the adhesive carried by the protective film from contamination.

An adhesive layer 24 (FIG. 1A) is provided on the surface of the protective film 20 that faces the base layer 16. This adhesive layer 24 initially adheres the base layer to the protective film, and then during application the adhesive stays with the protective film and allows the protective film to be removably adhered to the lens. Because the adhesive layer 24 will be present on the lens, the adhesive used is optically transparent and is formulated to be easily removable from the lens by the user, without leaving an adhesive residue and without damaging the lens. It is also generally preferred that the adhesive provide an airtight and watertight bond with the lens, particularly when the eyewear is to be used in an outdoor environment. Adhesive layer 24 is also preferably formulated to contribute to optical clarity by preventing creasing or visible marks from application of pressure while applying the protective film to the lens.

The application layer is adhered to the protective film by a thin layer 21 of a low adhesion pressure sensitive adhesive provided on the application layer. This adhesive layer is configured to have sufficiently low adhesion to allow the application layer to be very easily stripped from the protective film, without removing the protective film from the lens, while having sufficiently strong adhesion to hold the application layer in place on the protective film during application of the protective film to the lens. The adhesive remains on the application layer when the application layer is removed, leaving the protective film substantially free of adhesive residue, i.e., such that the surface is non-tacky and the transparency of the protective film is not impaired.

In some cases, the protective film includes at least one hard, scratch resistant coating 15, as shown in FIG. 1A. For example, coating 15 may be an optically clear hard coating for plastic films, such as the UV curable coatings commercially available from Dymax Corporation, or other hard coating such as those well known in the plastic film art. Some coatings have a pencil hardness, measured by ASTM D3363-05(2011)e2, of at least 4H, and in some cases at least 5H. This hard coating layer is optional and may be omitted in some applications, e.g., if use conditions are not harsh or if the protective film will be replaced after only a short use period. Whether or not a hard coating is included will also depend on the material of which the protective film is formed; some films, for example those formed of thermoplastic elastomers, are sufficiently soft and/or resilient to resist scratching without a hard coating.

The application tabs 14, 18, allow the protective film 20 to be positioned on a lens 28 (FIG. 2) without the user's fingers contacting the adhesive layer 24 or leaving fingerprints on either surface of the protective film. The application layer 12 allows the protective film to be applied to the lens without bubbles or creases being present between the lens and the protective film, and without dust or other debris being trapped under the protective film. The application tabs provide the user with a portion to grasp, and may include indicia (e.g., "1" and "2", as shown, or instructions, such as shown in FIGS. 3B and 3D) to help the user apply the protective film. For example, the numbering on the tabs in FIG. 1 indicates to the user which layer should be removed first. The application tabs also assist the user with repositioning the protective film if the user does not like how it is aligned on the lens, and/or lifting a portion of the film to remove trapped debris or air.

The protective film is configured to be conformable to the lens shape, and thus may be more or less flexible depending on the complexity of the shape. For example, generally a stiffer film may be used if the lens is flat or curved in only a single direction than if the lens is curved in more than one direction (e.g., a spherical lens) or has other characteristics that require a very conformable film. The protective film is also configured to provide the desired degree of protection to the lens, which will depend on the operating environment (ski slope, desert conditions, industrial use, etc.) and desired usable life. Because it is the layer that will remain on the lens, the protective film is transparent, and preferably has optical characteristics that are matched to or compatible with those of the lens. The protective film may include one or more coatings, in addition to or instead of the hard coating, including water-repelling coatings (e.g., oleophilic coatings), scratch resistant coatings, anti-glare coatings, privacy coating, polarization, mirror or tinted coatings, statically charged (dust repelling) coatings, flame or heat resistant coatings, and self-healing coatings. The coating layer(s) can be customized to a particular application, e.g., flame or heat resistant coatings for fire fighting or welding applications, or dust-repelling coatings for use in arid or dusty environments.

The application layer generally needs to be sufficiently soft and flexible to conform to the lens during application, while providing enough structural stability to the protective film to prevent wrinkling and creasing of the protective film during application.

The base layer is the thickest, most rigid layer, and is generally sufficiently stiff to prevent bending or flexing of the system in more than one direction during shipping and storage.

The application and base layers do not need to be transparent, although it may be desirable for the application layer to have some transparency to allow visualization of the underlying protective film during application. Either or both of the layers may be provided with graphics or other indicia, e.g., advertising or marketing information. In some cases, even the protective film may include graphics or branding information, e.g., a small logo in one corner as is often the case with branded sunglasses.

Figure 2:
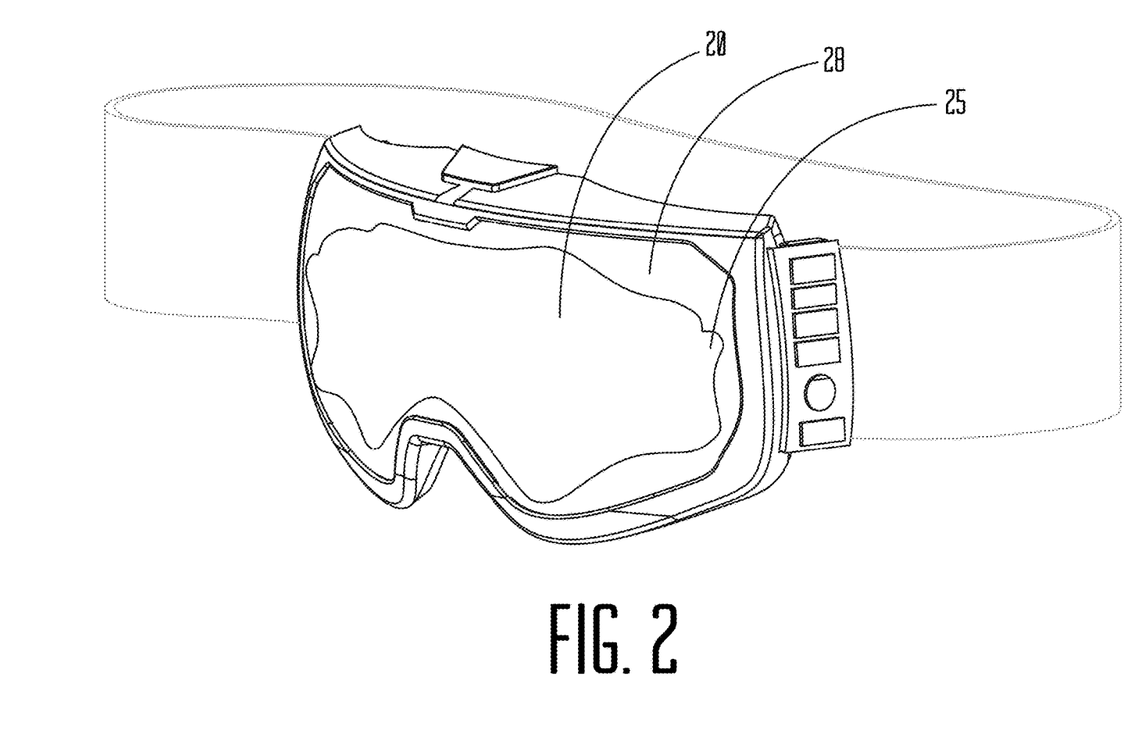
FIG. 2 is a perspective view of the protective film of the eyewear protection system shown in FIG. 1, in use on the goggles.
Figure 2A:
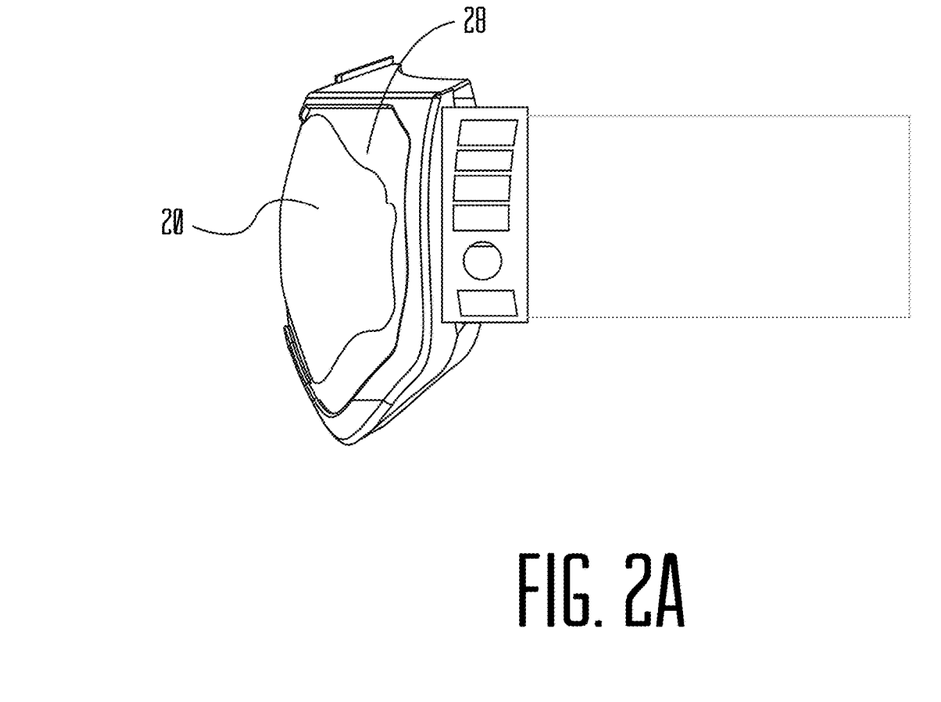
FIGS. 2A and 2B are side and top views, respectively, of the protective film in use, illustrating the "spherical" shape of the goggle lens.
Figure 2B:
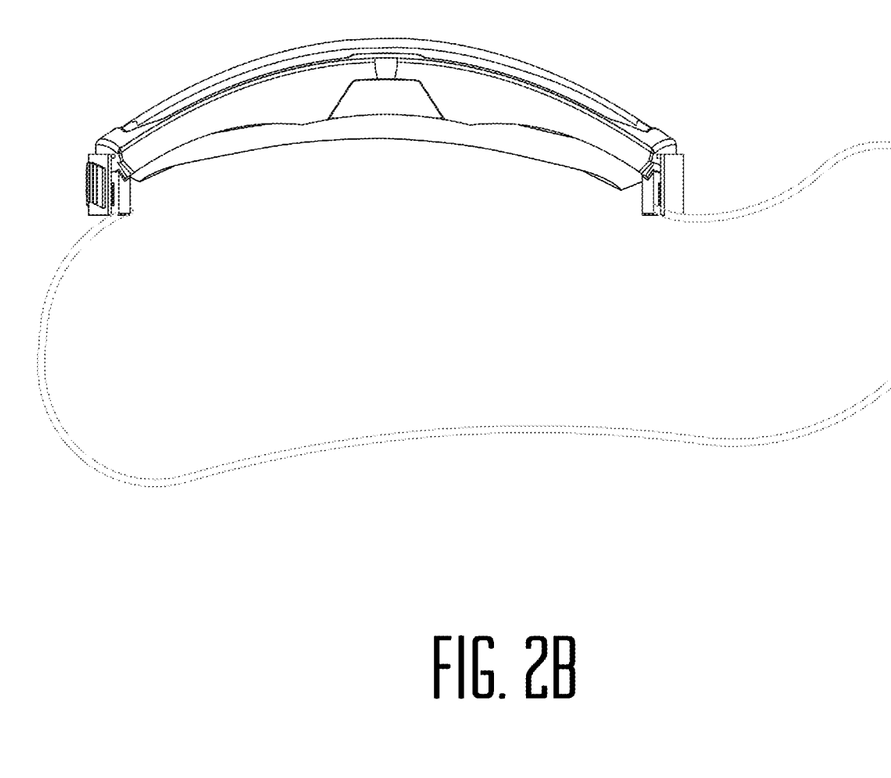

Referring to FIG. 2, when the system is to be used on a spherical lens, it is generally preferred that the peripheries of the protective film and the application layer be curved. This helps to prevent bunching and creasing of the edge of the protective and application layers as the system is applied to the lens. The protective film may include a tab 25 (FIG. 2) that allows the user to more easily slip a fingernail under the film to detach it from the lens. For ease of manufacturing it is generally preferred that the base layer have the same outline as the other layers; however, if desired the base layer can have a different shape, so long as it adequately supports the protective film and is removable therefrom by the user.

Figure 4:
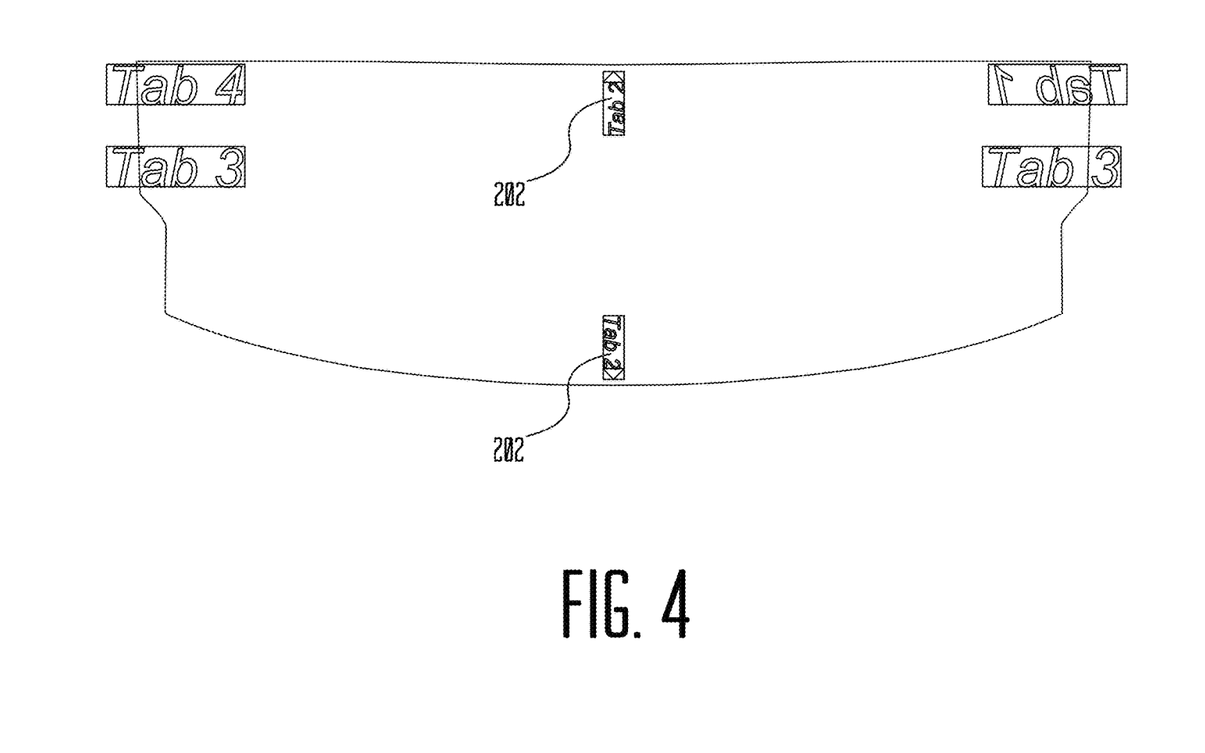
FIG. 4 is a front view of an eyewear protection system having an alternative shape.
Figure 5:
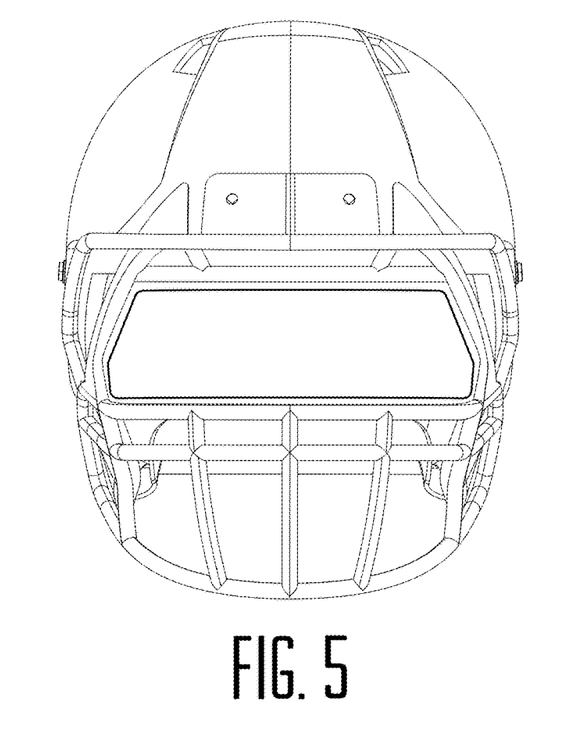
FIG. 5 is a front view of a protective film of an alternative eyewear protection system, having a different shape, positioned on a football helmet visor.

Examples of protective films applied to non-spherical lenses are shown in FIGS. 4 and 5. It is preferred that the protective film be sized so that it will fit within the frame of the eyewear and not obscure vents or cover the frame or other non-lens portions of the eyewear.

Figure 6:
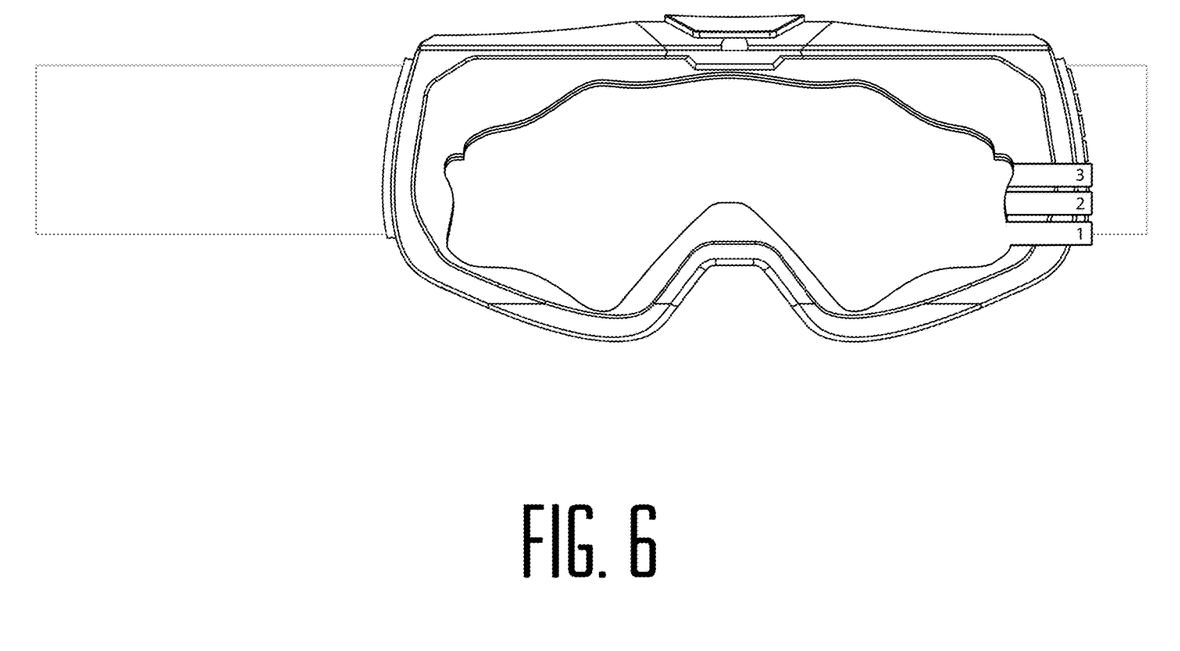
FIG. 6 is a front view of an alternate embodiment in which a protective film having multiple protective layers is used.

An example of an implementation in which the protective film has multiple protective layers is shown in FIG. 6. In the embodiment shown in FIG. 6, the protective layers have clear tabs, labeled 1, 2, 3, disposed outside of or at the edge of the user's field of vision. These tabs allow the user to sequentially peel off each layer as the layer becomes scratched or a fresh layer is desired.

Applying the Protective Film

Figure 3A:
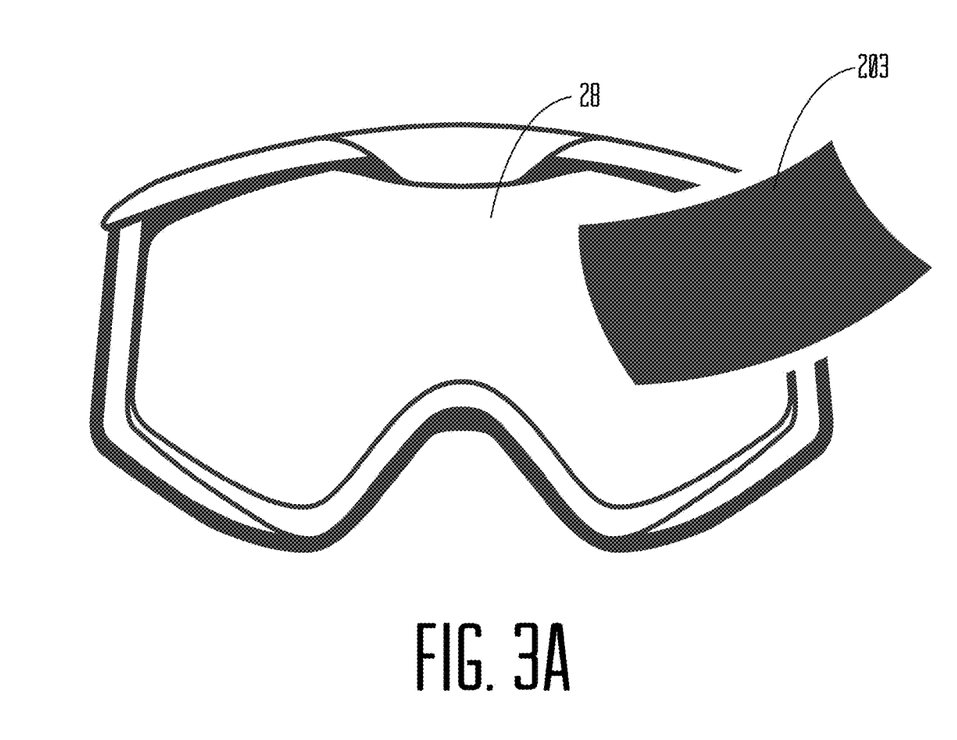
FIGS. 3A-3E are diagrammatic views showing steps in the application of the lens protection system shown in FIG. 1 to a pair of ski goggles.
Figure 3B:
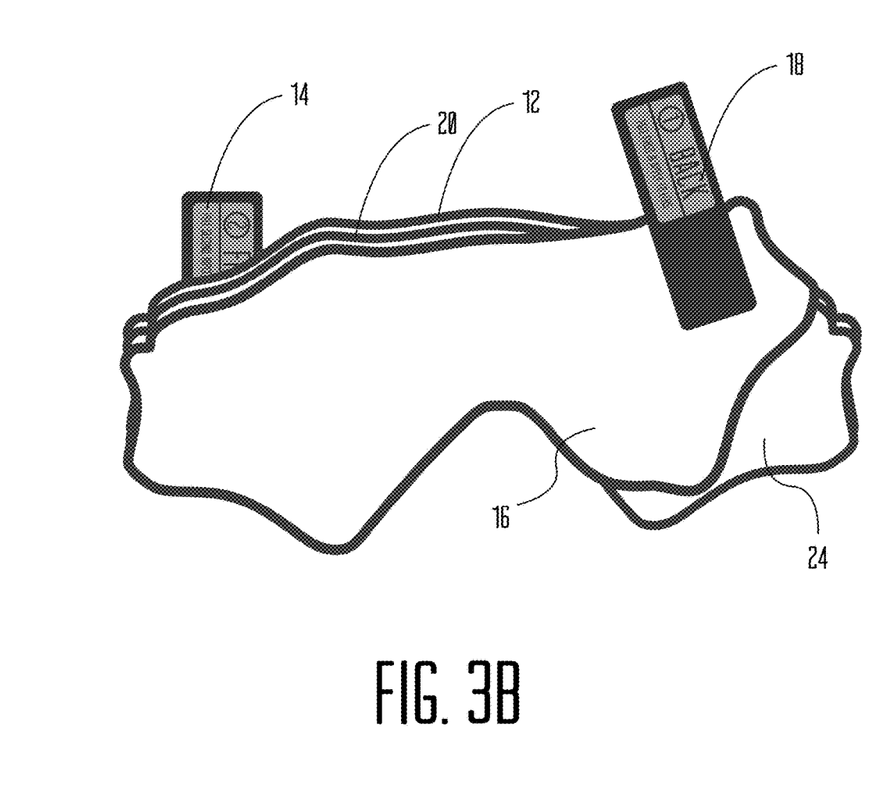
Figure 3C:
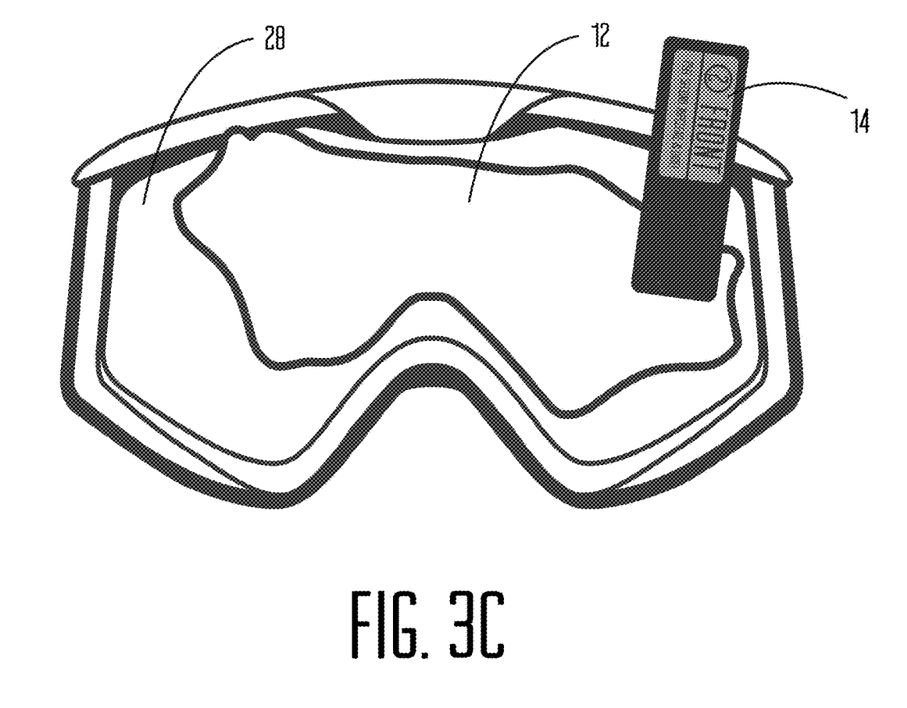
Figure 3D:
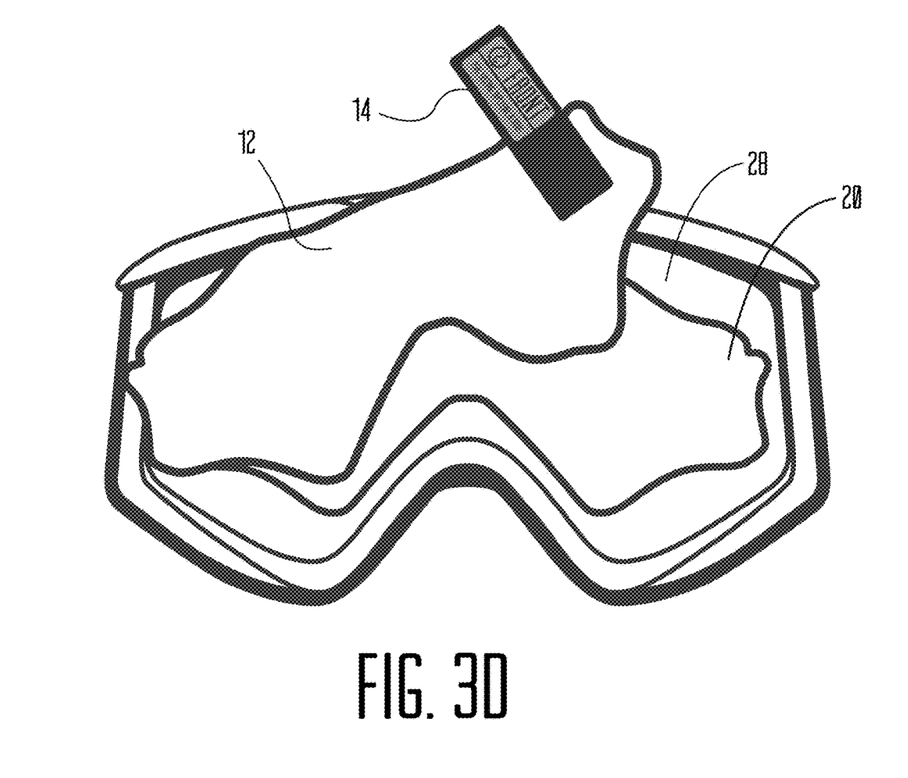
Figure 3E:
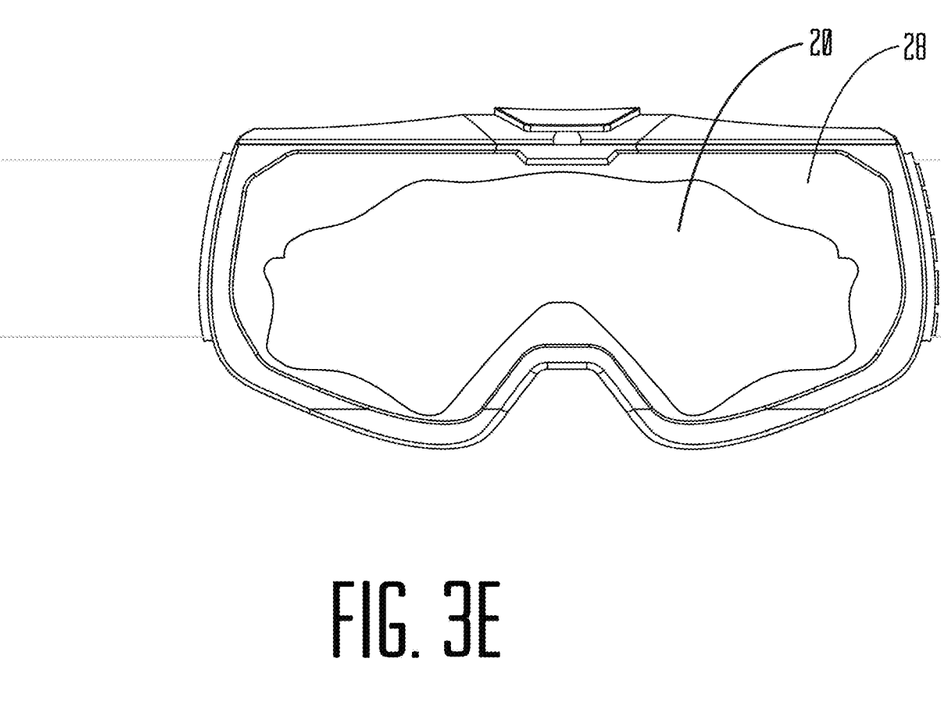

The protective film is applied to the lens as shown in FIGS. 3A-3E. First, it is important to clean the lens (FIG. 3A.) Once the lens is clean and substantially free of dust and debris, the user peels off the base layer (FIG. 3B), holding the system by the two tabs 14, 18. This exposes the adhesive layer 24 on protective film 20. The user is then left holding the application layer 12 and the attached protective film 20 by the application tab 14. (Or, in the case of a large protective film, the more substantial tabs 3, shown in FIG. 4.) The user lines the layers up with the goggle in the desired orientation, and then gently touches the adhesive layer 24 of the protective film 20 to the goggle surface (FIG. 3C). Next, starting from the middle, the user uses a soft cloth to press the application layer towards the lens surface, adhering the protective film to the surface while pushing any trapped air outwards from the center. If necessary, the application layer and attached protective film can be peeled up during application to remove any trapped air or dust particles. Last, the user grasps the application tab of the application layer and peels the application layer from the protective film (FIG. 3D), leaving the protective film firmly attached to the lens surface by the adhesive 24 (FIG. 3E). The outer surface of the protective film is smooth and non-tacky, due to the attachment of the application layer to the protective film by pressure sensitive adhesive 21, which stays with the application layer when it is removed.

In some implementations, the system includes tools and instructions for cleaning the lens so it is dust and dirt free and to assist the user in applying the protective film to the lens. For example, the system may include application instructions, an alignment sticker (e.g., centering stickers 202 provided on the application layer, as shown in FIG. 4), a wet cleaning wipe for cleaning the lens (e.g., wipe 203 in FIG. 3A), a microfiber cloth for pressing the application layer towards the goggle surface, and a dust removal sheet (for dust removal before application) and/or a dust removal sticker to help the user remove any dust or debris particles that are trapped during application (by peeling back the layers and dabbing the surface with the sheet before reapplying the layers). These components may be sold or otherwise supplied separate from the eyewear protection system, e.g., the dust removal sheet, dust removal sticker(s), and in some cases the microfiber cloth can be supplied as a separate cleaning kit.

Once it is applied, the protective film will stay in place until removed by the user. In some implementations, the adhesive provides a watertight and airtight seal between the lens and the protective film that will hold the protective film securely in place under whatever environmental conditions are encountered. When the user considers the protective film to be in need of replacement (e.g., due to scratching), the user gently inserts a fingernail under an edge of the protective film (e.g., under tab 25 in FIG. 2), peels back the layer, and strips it from the lens. The adhesive remains with the protective film, leaving the lens free of adhesive residue. The user can then replace the protective film by repeating the steps described above.

The time that the protective film may be used on a lens prior to removal and replacement will vary depending on a variety of factors, including the requirements of the user and the usage environment. For some applications the protective film may be used for three months or more of daily use of the eyewear, while in other scenarios it may be desirable to replace the protective film after a few uses or even a single use of the eyewear. Advantageously, the system is easy to apply and relatively inexpensive, and thus a new protective film can be applied as often as desired.

If the protective film is made up of multiple protective layers, successive layers can be removed as needed, prior to applying a new protective film to the lens. This may be more convenient for users who will need to frequently refresh the lens surface, e.g., high performance athletes or workers in harsh environments.

Materials

The application layer will generally be formed of a flexible thermoplastic sheet material, for example a polyethylene terephthalate (PET) polymer. Other flexible thermoplastics may also be used. It is generally preferred that the material be one to which pressure sensitive adhesives will adhere. In some implementations, e.g., when the system is to be used on a spherical lens, the material has a low durometer, e.g., less than 60 Shore D or even less than 40 Shore D, for example from about 10 to 60 Shore D. In this case, the PET may be formulated with additives, e.g., plasticizer, to reduce its hardness. This low durometer rating provides the application layer with sufficient flexibility to allow it to conform to a curved or spherical (double-curved) lens during application of the protective film. The application layer is generally transparent or translucent to allow the lens surface to be seen during application, but could be opaque if desired. The thickness of the application layer will depend on whether the system is being applied to a spherical goggle—in which case the application layer needs to be sufficiently thin to conform to the shape of the lens along with the protective film—or another shape of lens, in which case the application layer can be thicker if desired. In some cases, the application layer has a thickness in the range of about 0.01 to 1 mm, e.g., from about 0.05 to 0.3 mm. If the lens is relatively flat or gently curved, the application layer can be thicker, with generally the only constraints being cost and optical clarity.

The application tab may be formed of the same material as the application layer, for example if it is desired that the application tab be integral with the application layer, or may be formed of a different material and bonded, e.g., adhered or welded, to the application layer. In the latter case, the application tab may be formed of a stiffer material to give the user a better grasp on the application layer, and/or may be formed of a material that is easy to print so that the indicia/instructions can be easily applied to the tab. If the application tab is formed integrally with the application layer the indicia/instructions may be applied by adhering a label to the tab.

The protective film is formed of a material that is highly transparent, and in some cases optically transparent. The preferred material for the protective film will depend on the shape of the lens to which the protective film will be applied. For spherical (double-curved) lenses it is generally preferred that the material be very flexible, to allow the layer to conform to the lens shape without any wrinkling or creasing and without trapping air bubbles. In such cases, a suitable material would be a thermoplastic urethane having a durometer of less than 90 Shore A, e.g., from about 10 to 60 Shore A and in some cases from about 40 to 60 Shore A. Other polymers may be used, for example other transparent thermoplastic elastomers, provided that they can be formulated to have sufficient conformability at the desired thickness.

If less conformability is required, e.g., if the system will be used on a single curved or flat lens, the material of the protective film may be somewhat less flexible. For such applications, a suitable material would be PET having a higher durometer, e.g., from about 20 to 60 Shore D. PET provides a good balance of conformability and durability, and is relatively low cost. Thermoplastic urethanes may also be used in these less demanding (conformability-wise) applications, though they tend to be more expensive. Other materials may also be used in some applications, for example transparent thermoplastics such as polycarbonate, polypropylene, and polyvinyl chloride. These relatively hard materials may not provide as much optical performance as PET, but may be desirable for use in harsh environments, e.g., industrial use. Other factors in material selection for the protective film include cost, ability of the adhesive layer 24 to adhere to the material, and optical clarity.

The protective film may in some cases have a thickness of less than 1 mm, e.g., less than 0.5 mm. In some implementations the thickness of the protective layer will be from about 0.01 to 1 mm, for example 0.04 to 0.40 mm. The thickness of the layer will depend upon the material used, the required durability and useful life of the layer, and the expected use conditions. For ski goggle protection, generally if PET is used, the protective film will be thinner, e.g., from about 0.04 to 0.1 mm, while if a thermoplastic urethane is used the layer will in some cases be thicker, e.g., about 0.15 to 0.25 mm. However, in some cases a thermoplastic urethane film could be used having a thickness of about 0.04 to 0.1 mm.

The protective film (either the base material of the film, or the hard coating applied to the base material) is preferably sufficiently scratch resistant to prevent scratching during the intended life of the protective film. In some cases, the protective film may be capable of passing the MIL-PRF-32432 abrasion resistance test when the protective film is mounted on a lens.

The base layer may be of any sheet material having sufficient stiffness to protect the other layers during shipping and storage. For example, the base layer may be formed of PET or other thermoplastic having a relatively high durometer, e.g., at least 30 Shore D, for example from about 30 to 90 Shore D. The base layer may also be formed of materials other than plastics, e.g., release papers. The base layer may have a thickness similar to that of the application layer, or may be thicker if desired. Generally, the only limitation on the thickness of the base layer is cost.

Adhesives

The adhesive that is carried by the protective film has the greatest adhesion strength, and if the eyewear lens is to be used in an outdoor environment is preferably formulated to provide a watertight seal between the protective film and lens. Suitable adhesives include, for example, pressure sensitive silicone adhesives such as those commercially available from Dow Corning, e.g., Dow Corning 7651 high performance silicone pressure sensitive adhesive. In addition to providing a good seal between the lens and protective film, preferred adhesives are optically transparent, and retain this transparency when pressure is applied to adhere the layer to the lens, are repositionable, will not damage the lens or remain on the lens when the protective film is removed, and adhere to the material used for the protective film. The peel strength of the adhesive is selected so that the protective film will remain on the lens during the intended use period, but can be removed by the user inserting a fingernail under the edge of the film and peeling the film back. In some cases, the adhesive layer 24 has a thickness of about 0.02 to 0.03 mm.

The adhesives used between the base layer and protective film and between multiple protective layers may in some cases be formulated to have lower peel strengths, and/or provided in a thinner layer, so that the layers can be easily separated. However, this is not always necessary, as the force applied to the top protective layer by peeling back the tab on that layer is potentially greater than the force that is indirectly applied to the protective film/lens interface during this procedure.

The adhesive provided between multiple protective layers should also be optically clear, but this is not a requirement for the adhesive layer 21, since this adhesive will be stripped away with the base layer rather than remaining on the lens during use.

In some cases, the adhesive used on the protective film is selected to allow the Ballistic Fragmentation performance of the lens to remain substantially unaltered after the lens has been exposed to the adhesive for a period of time, e.g., at least 1 day, at least 1 week, or at least 1 month.

Other Embodiments

A number of embodiments have been described. Nevertheless, it will be understood that various modifications may be made without departing from the spirit and scope of the disclosure.

For example, the number of protective layers that make up the protective film, can be changed as desired to suit particularly applications. For example, while three layers are shown in FIG. 6, two, four, five, six, or more protective layers can be adhered together to form the protective film. The tabs used to peel off sequential layers may be clear, as discussed with reference to FIG. 6, or may be translucent or opaque, so long as they do not unduly interfere with the user's vision.

In some implementations, the adhesive used to adhere the protective film to the lens, and/or the adhesive used to adhere the protective layers together, may be replaced by a different (non-silicone based) adhesive and/or by electrostatic charge.

While goggles have been discussed above, the systems may be used on many other types of eyewear. For example, the system may be shaped to fit on the eyeshield of a helmet, such as the football helmet shown in FIG. 5, or other types of eye protective lenses such as the separate lenses of sunglasses or safety glasses.

While the systems are designed primarily for use on eyewear, they may be used in other applications, for example as screen protectors for cameras and electronic devices such as smartphones which need protection of their optical grade surfaces and lenses.

Accordingly, other embodiments are within the scope of the following claims.

What is claimed is:

1. An eyewear protection system comprising:
an optically transparent protective film, shaped to fit within a frame in which an eyewear lens is mounted, and comprising a sheet material carrying, on an adhesive side, a layer of an optically transparent pressure sensitive adhesive having a composition selected to allow the protective film to be temporarily adhered to an eyewear lens and later removed therefrom, and
a base layer, adhered to the adhesive side of the protective film,
wherein the base layer is constructed such that it is removable from the protective film, the base layer comprises a flexible sheet material, the base layer is adhesive-free on both of its broad surfaces, and is of a different thickness than the protective film, the protective film comprises a polymer selected from the group consisting of thermoplastic urethanes and polyethylene terephthalate polymer, and the base layer comprises polyethylene terephthalate.

2. The eyewear protection system of claim 1 wherein the protective film comprises two or more layers of sheet material adhered to each other by a pressure sensitive adhesive.

3. The eyewear protection system of claim 1, further comprising an application layer that is adhered to the protective film by a pressure sensitive adhesive carried by the application layer.

4. The eyewear protection system of claim 1 wherein the adhesive carried by the protective film comprises a silicone.

5. The eyewear protection system of claim 1 wherein the adhesive carried by the protective film provides a watertight seal against the lens surface.

6. The eyewear protection system of claim 1 wherein the layer of adhesive carried by the protective film has a thickness of from about 10 to 30 µm.

7. The eyewear protection system of claim 1 wherein the protective film has a thickness of from about 0.01 to 1.0 mm.

8. The eyewear protection system of claim 7 wherein the protective film is shaped to fit a spherical goggle lens.

9. The eyewear protection system of claim 8 wherein the protective film comprises a thermoplastic urethane.

10. The eyewear protection system of claim 1 wherein the protective film carries a scratch resistant coating layer on a surface opposite the surface on which the adhesive is carried.

11. The eyewear protection system of claim 1 further comprising an application tab extending from the base layer.

12. The eyewear protection system of claim 1 further comprising an application layer adhered to the opposite side of the protective film.

13. The eyewear protection system of claim 12 wherein the application layer comprises polyethylene terephthalate.

14. The eyewear protection system of claim 2 wherein the protective film comprises five or more layers of sheet material adhered to each other by a pressure sensitive adhesive.

15. The eyewear protection system of claim 2 wherein the pressure sensitive adhesive adhering the layers of sheet material together has an adhesion strength less than or equal to that of the adhesive adhering the protective film to the lens.

16. The eyewear protection system of claim 12 wherein the application layer includes a graphic or branding information printed on a surface of the application layer.

17. The eyewear protection system of claim 1 wherein the protective film includes a graphic or branding information printed on a surface of the protective film.

18. The eyewear protection system of claim 1 wherein the protective film flexibly conforms to an eyewear lens having a curved outer surface.

19. The eyewear protection system of claim 1 wherein the base layer is configured to be stripped from the protective layer prior to use of the system.

20. The eyewear protection system of claim 1 wherein the polyethylene terephthalate of the base layer has a durometer of from about 30 to 90 Shore D.

* * * * *